United States Patent [19]

Tunc

[11] Patent Number: 4,905,680
[45] Date of Patent: Mar. 6, 1990

[54] ABSORBABLE BONE PLATE

[75] Inventor: Deger Tunc, East Brunswick, N.J.

[73] Assignee: Johnson & Johnson Orthopaedics, Inc., New Brunswick, N.J.

[21] Appl. No.: 224,047

[22] Filed: Jul. 25, 1988

Related U.S. Application Data

[63] Continuation-in-part of Ser. No. 923,234, Oct. 27, 1986, abandoned.

[51] Int. Cl.⁴ .............................................. A61B 17/58
[52] U.S. Cl. ........................................ 606/69; 606/77
[58] Field of Search ......... 128/92 YP, 92 YL, 92 YQ, 128/92 YG, 92 YR, 92 YN

[56] References Cited

U.S. PATENT DOCUMENTS

| | | | |
|---|---|---|---|
| 1,105,105 | 7/1914 | Sherman | 128/92 YP |
| 3,463,148 | 1/1966 | Treace | 128/92 YP |
| 3,528,085 | 9/1970 | Reynolds, Jr. | 128/92 YP |
| 4,219,015 | 8/1980 | Steinemann | 128/92 YP |
| 4,403,607 | 9/1983 | Woo et al. | 128/92 YP |
| 4,411,027 | 10/1983 | Alexander et al. | 623/16 |
| 4,429,690 | 2/1984 | Angelino-Pievani | 128/92 YP |

OTHER PUBLICATIONS

Vitallium Surgical Appliances, 128 92YP, Mar. 1948, p. 7.

*Primary Examiner*—Robert A. Hafer
*Assistant Examiner*—Kevin G. Rooney
*Attorney, Agent, or Firm*—Michael Q. Tatlow

[57] ABSTRACT

An absorbable bone plate resistant to breakage fabricated with such interrelated dimensions that the highest stresses developed along the length of the plate when the plate is implanted are relatively constant and do not vary by more than 20% and preferably do not vary by more than 10%.

8 Claims, 3 Drawing Sheets

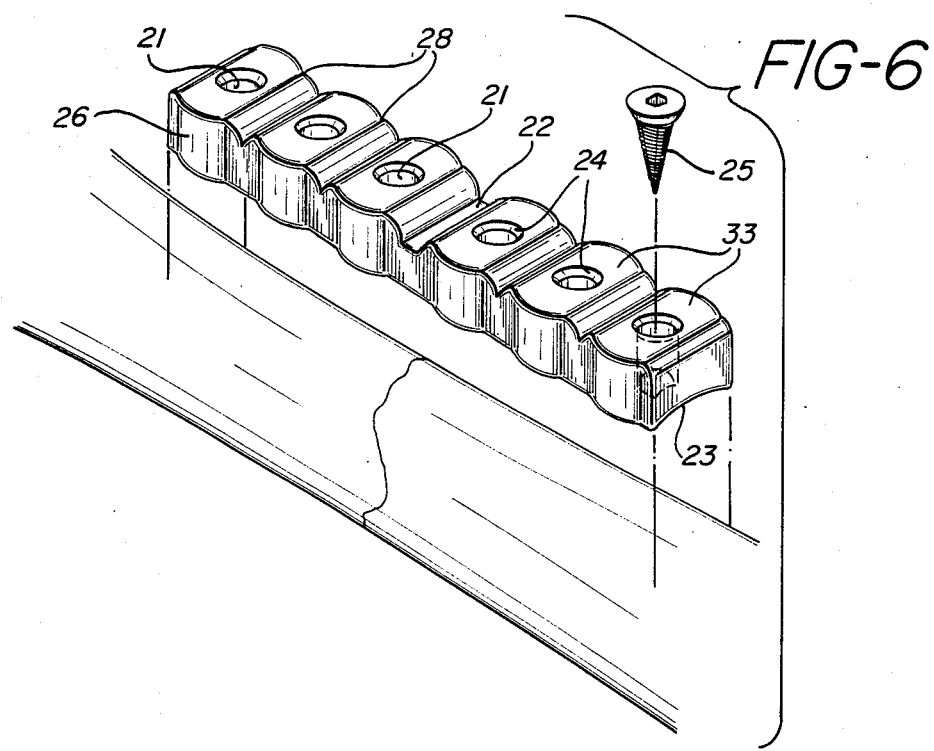

ABSORBABLE BONE PLATE

This application is a continuation-in-part of application Ser. No. 923,234 filed Oct. 27, 1986.

The present invention relates to a bone plate used as an aid for osteosynthesis and which is made of a material which will be absorbed in the body.

BACKGROUND OF THE INVENTION

Metallic bone plates and screws have been used for sometime in osteosynthesis to approximate fractured or broken bones in the body. These plates are generally made of materials such as stainless steel, chrome cobalt, titanium and various alloys of such metals. The bone plates are used to hold fractured bones in position so that they may heal in a proper manner. The bone plates offer advantages over the immobilization of the bone using only simple casting techniques. The use of internal fixation eliminates long periods of casting and allows early active joint movement which provides greater or earlier mobility to the patient.

It has been suggested that it would be desirable to form such bone plates from materials which would be absorbed by the body to eliminate the necessity of a second surgical procedure to remove the bone plates after the bone has healed. An absorbable polymer capable of being fabricated into a bone fixation device or bone plate is disclosed in U.S. Pat. Nos. 4,539,981 and 4,550,449.

Bone plates fabricated from metal have been made in various designs. Generally, the design consists of a bar of the particular metal which is curved on the surface which will be placed against the bone. The plate has a number of screw holes in the plate and screws are introduced through the holes to secure the plate to the bone U.S. Pat. No. 3,463,148 discloses a metallic bone plate which has a substantially constant cross-sectional area. The plate has screw holes through the plate which are spaced on either side of a longitudinal center line. The metal in the area of the screw holes is thicker than the area of the metal between the screw holes.

U.S Pat. No. 4,219,015 discloses a metallic bone plate in which the bending resistance moment, $W=I/e$, is relatively constant throughout the plate and the stress is variable. Specifically, the lower limiting value of the bending resistance moment is, at most, 30% smaller than the upper limiting value. In the plate of the present invention the stress is relatively constant and the bending resistance moment is variable.

U.S. Pat. No. 4,429,690 discloses a metal plate for the fixation of broken bones comprising two longitudinal bars joined by an array of humped bridges or crossed brackets evenly spaced along the length of the bars and having holes to set cortical screws. The design of this plate is indicated to resists fracture to a greater degree than the plates previously used.

All of the above mentioned bone plates are designed to be fabricated from a relatively strong metal, such as stainless steel, chrome cobalt or titanium. The absorbable polymer from which the present bone plates are made does not have the strength of these metals. The strength of the absorbable polymer is significantly less than the strength of the metal from which the metallic bone plates are fabricated and, for that reason, the design of the metallic bone plates are not necessarily usable in a bone plate fabricated from an absorbable polymer. Although it would be theoretically possible to simply increase the thickness of an absorbable bone plate to compensate for the difference in strength when compared to a metallic bone plate, such simple modifications are not desirable. It is necessary to minimize the thickness of any bone plate so that the plate will not sit too high on the bone and cause difficulty in the coverage of the bone plate with soft tissue following a surgical procedure. If the plate is too thick, it simply cannot be used. Similarly, anatomical restrictions also limit the width of a bone plate. The bone plate cannot be too much wider than the width of the bone for which it is designed to repair.

SUMMARY OF THE INVENTION

The present invention provides a bone plate made from absorbable polymer which can be used in the fixation of bones without fear of the bone plate breaking.

The present bone plate is constructed so that the stresses developed when the bone plate is used are relatively constant and are below the yield strength of the absorbable polymer from which the plate is fabricated. To maintain the stresses relatively constant, the area of the plate around the screw holes is reinforced in both the width and height of the plate. The reinforcement areas are optimized to insure that when the plate is subjected to the stresses generated upon fixation of the bone, the plate will not break and that the dimensions of the plate will be a minimum thickness and width.

BRIEF DESCRIPTION OF THE DRAWINGS

FIG. 6 is a perspective view of another embodiment of the bone plate of the present invention.

FIG. 7 is a top plan view of the bone plate shown in FIG. 6.

FIG. 8 is a side elevation of view of the bone plate shown in FIG. 6.

FIG. 9 is a cross-sectional view taken along lines 9—9 of FIG. 7.

FIG. 10 is a cross-sectional view taken along the lines 10—10 of FIG. 7.

DETAILED DESCRIPTION OF THE INVENTION

The bone plate of the present invention is made from the absorbable polylactide polymer disclosed in U.S. Pat. Nos. 4,539,981 and 4,550,449. The polymer is a polylactide polymer which has a very high molecular weight and is strong enough to be fabricated into bone plates, screws and other internal fixation devices. The polymer will maintain its strength for a long enough period of time for the bone, onto which it is placed, to heal and it will be absorbed by the body over an extended period of time. As the polymer is absorbed, the bone plate will lose its strength. At the same time, the bone will be healing and be capable of assuming its normal load. There is no benefit to the patient in maintaining the bone plate supporting the fracture site after the bone has healed. The presence of metal bone plates on the bone after the bone has healed is considered to be detrimental because of possible corrosion and because the rigid metal plates prevent the bone from responding to normal load carrying activity. Metal plates are generally surgically removed between one and one-half to two years after implantation. The bone plate of the present invention could also be fabricated from other absorbable polymers which have the necessary strength and which have the characteristics of maintaining a strength in the body for the required time period.

The particular design of the bone plate of the present invention is such that the bending stress at any point along the length of the bone plate does not exceed the level of stress through the center of a screw hole where the plate is fixed to the bone. The bending stress is determined by fixing the bone plate at one screw hole and bending the plate downward by loading weight at the next screw hole. In the plate of the present invention, the maximum stress at any point of the plate should not exceed the yield strength of the polymer when the bending load applied by the tightening of the screw is 300 Newtons. The Yield strength of the polylactide polymer is 55 mpa.

In addition, the stresses developed when the plate is loaded should be relatively constant throughout the plate. By relatively constant is meant that the stress, developed at the screw hole does not vary by more than 20%, preferably not more than 10%, from the highest stress at any other point in the plate when the plate is loaded by affixing the plate to a bone.

The area around the screw hole is reinforced both at the top of the screw hole and along the sides of the bone plate. The reinforcement is minimized in both the top and side to insure that the total bone plate is not excessively wide or thick.

Figure 1:
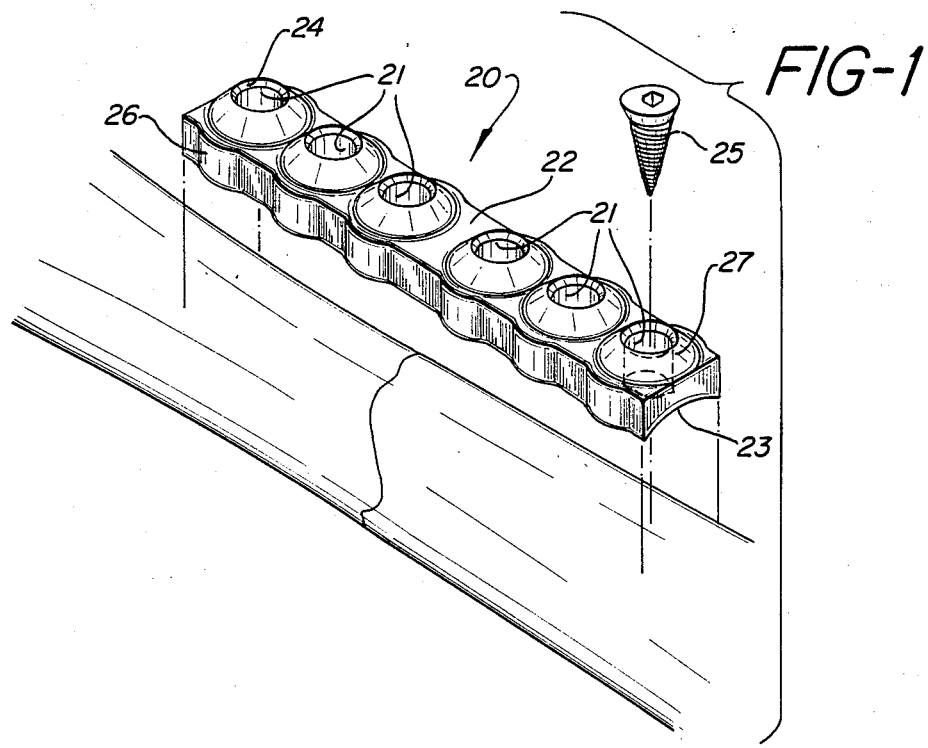
FIG. 1 is an perspective view of one of the embodiments of the bone plate of the present invention.
Figure 2:
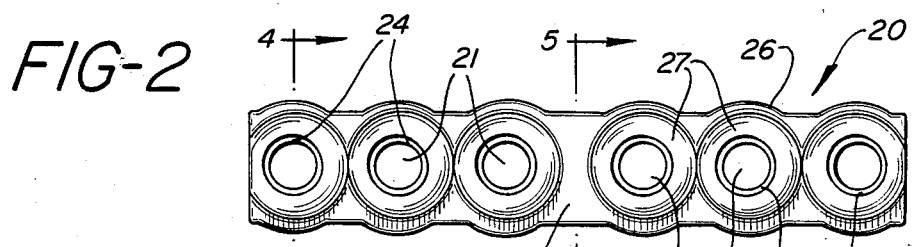
FIG. 2 is a top plan view of the bone plate shown in FIG. 1.
Figure 3:
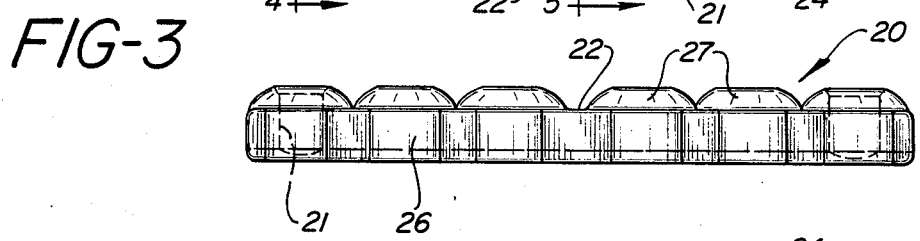
FIG. 3 is a side elevational view of the bone plate shown in FIG. 2.
Figure 4:
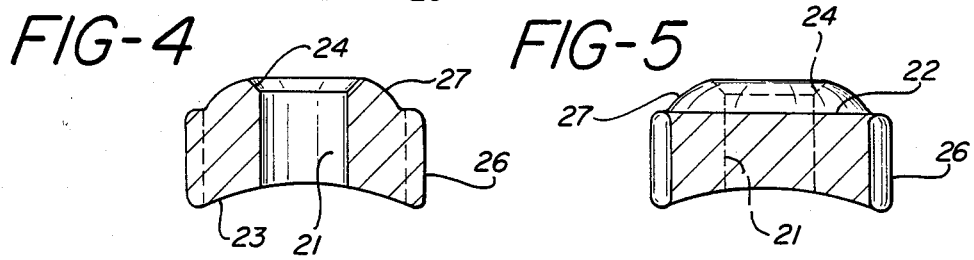
FIG. 4 is a cross-sectional view taken along lines 4—4 of FIG. 2.
Figure 5:
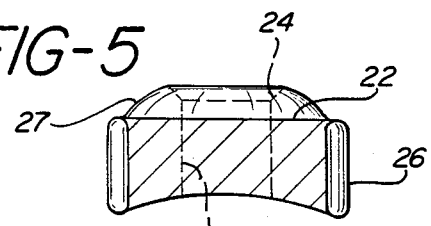
FIG. 5 is a cross-sectional view taken along lines 5—5 of FIG. 2.
Figure 11:
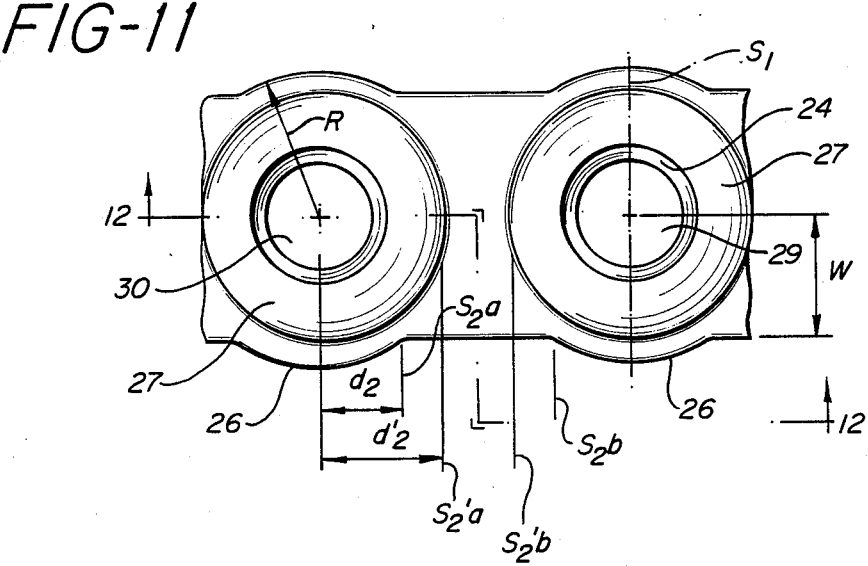
FIG. 11 is an enlarged fragmenting top view of the bone plate of FIG. 1.
Figure 12:
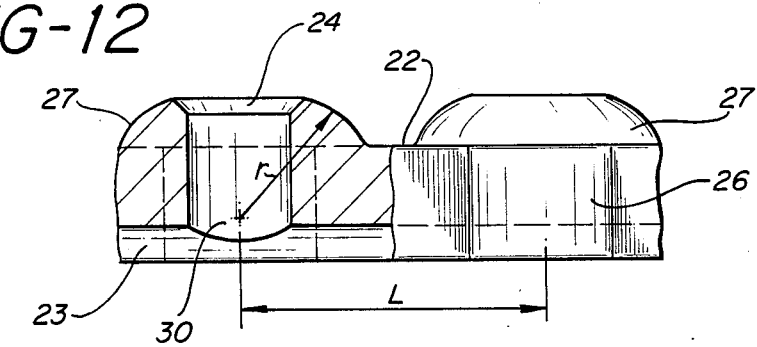
FIG. 12 is a partial cross-sectional view taken along lines 12—12 of FIG. 11.
Figure 13:
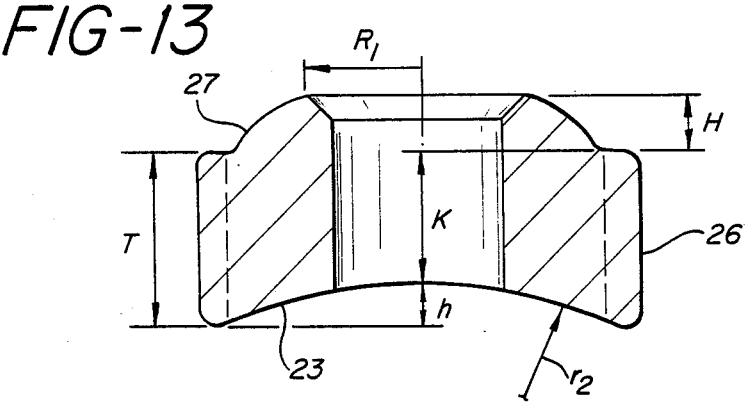
FIG. 13 is an enlarged cross-sectional end view of the plate similar to FIG. 4.

In order to provide a plate of constant strength, it is necessary to maintain a relationship between certain dimensions of the plate and in particular the reinforced areas of the plate. The dimensions are shown in FIG. 11-13 using the following designations:

T is the unreinforced plate thickness measured at the side edge of the plate

W is one half the width of the unreinforced plate

H is the height of the top reinforcement measured from the unreinforced top surface of the plate R is the radius of the side reinforcement of the plate measured from the centerline of a screw hole r is the radius of the top reinforcement measured along the centerline of a screw hole $d'_2$ is the distance from the centerline of the screw hole to the point where the top reinforcement intersects the unreinforced top of the plate $d_2$ is the distance from the transverse centerline of the screw hole to the point where the side reinforcement intersects the unreinforced side of the plate L is the distance between adjacent screw holes measured from the screw hole centerlines $R_1$ is the radius of the countersink measured from the screw hole centerline $r_2$ is the radius of curvature of the bottom of the plate k is the minimum unreinforced thickness of the plate measured from the top of the radius of curvature of the bottom of the plate to the unreinforced top of the plate h is the difference between T and k.

In order to provide a plate with acceptable strength and optimum thickness, the following relationships must be met.

$$\sqrt{W^2 + R_1^2} \leq R \leq \sqrt{W^2 + (L/2)^2} \quad (a)$$

$$r \geq \sqrt{R_1^2 + H} \quad (b)$$

$$d'_2 > d_2 \quad (c)$$

$$d_2 = \sqrt{R^2 - W^2} \quad (d)$$

$$d'_2 = \sqrt{r^2 - [\sqrt{r^2 - R_1^2} - H]^2} \quad (e)$$

$$h = r_2 - \sqrt{r_2^2 - W^2} \quad (f)$$

The bone plate of the present invention may take different configurations. The plate shown in FIGS. 1-5 is one typical configuration and the plate shown in FIGS. 6-10 is a second typical and preferred configuration. Both of these plates can be considered to have a generally rectangular main portion with a curved or arcuate lower surface to be placed on the surface of the bone to be repaired. There are reinforcing areas in the side and top of the plate around the screw holes. The difference between the plates of FIG. 1-5 and FIG. 6-10 is the shape of the top reinforcement area. The bone plate 20 shown in FIGS. 1-5 is of a sufficient length to bridge the fracture site in the bone. The plate has a number of screw holes 21 on either side of a center section 22. The lower surface 23 is arcuate to allow the plate to better fit the curvature of the bone to which the plate is attached. The unreinforced thickness of the plate is shown as T in the drawing FIG. 13 and the top reinforcement is shown as H. The unreinforced half width of the plate is shown as W and the radius of reinforced width as R in the drawings of FIG. 11. There is a countersink 24 at the top of the screw holes 21 so the screw 25 may be almost flush with the upper surface of the plate when the plate is attached to the bone. For purposes of orientation, the centerline of the screw hole 29 or 30, in the direction through the thickness of the plate is referred to as the screw hole centerline. The centerline of the screw hole in the direction perpendicular to the length of the plate is referred to as the transverse centerline.

The side reinforcing area can be considered to be a right circular cylinder of a radius R, FIG. 11, which is concentric with the screw hole and which intersects the side of the rectangular main portion of the plate at a distance $d_2$ from the transverse centerline of the screw hole. The top reinforcing area can be considered to be a portion of a sphere, which has a radius which intersects the top of the unreinforced rectangular portion of the plate at a distance $d'_2$ from the screw hole centerline of the screw hole. The dimension of $d'_2$ is greater than the dimension of $d_2$ in order to obtain the desired properties of the plate. The top portion of the sphere is flattened at the countersink 24 to reduce the total height of the plate. The plate shown in FIGS. 6-10 differs from the plate shown in FIGS. 1-5 only in the shape of the top reinforcing element. The top reinforcing element in the plate of FIGS. 6-10 can be considered to be a portion of a right circular cylinder with its axis perpendicular to the length of the plate and extending through the side edges of the plate. The upper portion of the cylinder is removed for the countersink 24 and the top of the reinforcement area 28 has a flat surface 33 to reduce the thickness of the plate.

The stresses that are developed when a bone plate is in use can be best explained with reference to FIGS. 11-13. A bone plate is affixed to a fractured bone on the tension side of the bone, i.e., on the convex side of the curve in the long dimension of the bone. In order to firmly affix the plate to the bone, the plate will be bent to conform to the curvature of the bone. The plate will be stressed as the screws are inserted into the bone. Assuming that the plate is first attached to the bone with a screw through screw hole 29, the maximum stress will be developed at the screw hole 29 when a screw placed through screw hole 30 is affixed to the bone. The side reinforcement 26 and the top reinforcement 27 prevents the plate from breaking at the screw hole 29. In the Examples that follow, the stresses are determined or calculated along various lines across the width of the plate where the plate is most likely to break when the plate is loaded as it is affixed to a bone. The line $S_1$ is located through the screw hole. The line $S_{2a}$ passes through the intersection of the side reinforcement and the unreinforced side of the plate around screw hole 30. The line $S_2'a$ passes through the intersection of the top reinforcement area and the unreinforced top of the plate around the screw hole 30. The line $S_2'b$ passes through the point where the top reinforcement around the next adjacent screw hole 29 intersects the unreinforced top of the plate. The line $S_2b$ passes through the point where the side reinforcement of the next adjacent screw hole 29 intersects the unreinforced side of the plate. In the Examples the plate is first fixed at screw hole 29 and the load is applied at screw hole 30.

Generally, bone plates have a length of between about 50 and 200 millimeters. The minimum length is dictated by the desirability to have at least four screw holes in the plate. There is no limitation on the maximum length of the plates other than the maximum length of a bone to be repaired. For most repairs, the bone plates will be between 50 and 200 millimeters in length. The width of the bone plate is dependent on the size of the bone to which the plate will be attached. Generally, the unreinforced width of the plates are between 5 and 15 millimeters. The unreinforced height of the plates of the present invention are between 4 and 10 millimeters. The unreinforced height is measured from the bottom of the plate to the unreinforced surface at the top of the plate. In order to obtain the desirable strength properties in the plates of the present invention, the reinforcement in the width of the plate should be between 1 and 4 millimeters. The reinforcement in the height of the plate should be between 1 to 5 millimeters depending on the unreinforced thickness of the plate.

The following Examples are show designs of various bone plates which are reinforced in different areas and show the effect of the reinforcement on the stresses that would be developed in the bone plate. The ultimate tensile strength of the polylactide polymer is about 70 MPA.

EXAMPLE I

Unreinforced 4 MM Thick Plate

The stress in a polylactide plate, 4.0 millimeters thick is calculated. The stress in the plate at a screw hole and the highest stress at any other point in the plate are calculated at different loads. The results are shown in the following Table:

| LOAD | Stress | |
|---|---|---|
|  | 300 N | 535 N |
| Screw Hole | 150.3 M Pa | 267 M Pa |
| Highest Stress at any other point | 59.7 M Pa | 106 M Pa |

The stress at the screw hole exceeds the yield strength of the polymer and the plate would fail at the screw hole if implanted.

EXAMPLE II

Unreinforced 6.4 Thick Plate

The stresses are calculated for a plate as in Example I. The plate has a uniform thickness of 6.4 millimeters. The results are shown in the following Table:

| LOAD | Stress | |
|---|---|---|
|  | 300 N | 535 N |
| Screw Hole | 66.4 M Pa | 118.2 M Pa |
| Highest Stress at any other point | 29.3 M Pa | 52.1 M Pa |

The stresses generated at the screw hole due to 300 N and at 535 N load are greater than the yield and the ultimate strength of the polymer.

EXAMPLE III

Plate with Top Reinforcement Only

The stresses are calculated for a bone plate having a thickness of 4 millimeters and additional thickness of 2.4 millimeters around the top of the screw holes. The results are shown in the following Table:

| LOAD | Stress | |
|---|---|---|
|  | 300 N | 535 N |
| Screw Hole | 66.4 M Pa | 118.2 M Pa |
| Highest Stress at any other point | 43.8 M Pa | 78.0 M Pa |

The stress generated due to 535 N loading around the screw hole is greater than the ultimate strength of the polymer.

EXAMPLE IV

Plate with Side Reinforcement Only

The stresses are calculated for a plate having a thickness of 4 millimeters and an additional thickness of 2.8 millimeters around the sides of the screw holes. The results are shown in the following Table:

| LOAD | Stress | |
|---|---|---|
| | 300 N | 535 N |
| Screw Hole | 100.3 M Pa | 178.6 M Pa |

The stresses exceeded the ultimate strength of the polymer.

EXAMPLE V

Top and Side Reinforced Plate

The stresses are calculated for a plate having a thickness of 4.0 millimeters and a reinforcement around the top of the screw hole of 2.4 millimeters and a reinforcement around the side of the screw hole of 2.8 millimeters. The results are shown in the following Table:

| LOAD | Stress | |
|---|---|---|
| | 300 N | 535 N |
| Screw Hole | 43.4 M Pa | 77.4 M Pa |
| Highest Stress at any other point | 43.8 M Pa | 78.0 M Pa |

The stresses in this plate are well balanced and within the yield strength of the polymer. A plate of this design would be suitable for use in fixation of bones.

EXAMPLE VI

Top and Side Reinforced Thin Plate

The stresses were calculated for a plate having a thickness of 3.0 millimeters, a top reinforcement of 2.4 millimeters and a side reinforcement of 2.8 millimeters. The results are shown in the following Table:

| LOAD | Stress | |
|---|---|---|
| | 300 N | 535 N |
| Screw Hole | 58.1 M Pa | 103.6 M Pa |
| Highest Stress at any other point | 70.5 M Pa | 125.6 M Pa |

In this plate, the stress in the unreinforced area of the plate exceeded the yield strength of the polymer.

EXAMPLE VII

Plate with Excess Reinforcement

The stresses were calculated for a plate having a thickness of 4 millimeters, a top reinforcement of 3.4 millimeters and a side reinforcement of 4.8 millimeters. The results are shown in the following Table:

| LOAD | Stress | |
|---|---|---|
| | 300 N | 535 N |
| Screw Hole | 27.1 M Pa | 48.3 M Pa |
| Highest Stress at any other point | 48.0 M Pa | 85.4 M Pa |

Although this plate is acceptable in terms of strength, it is anatomically less desirable since it is thicker and wider than the plate of Example V.

EXAMPLE VIII

A plate was fabricated as in Example I in the form shown in FIGS. 1-5 of the drawings. The unreinforced thickness was 5.0 millimeters, the top reinforcement was 4.8 millimeters in maximum thickness and the side reinforcement was 3.0 millimeters in width. The stress was determined at a load 300 N and of 535 N as in Example I and the results as shown in the following Table:

| LOAD | Stress | |
|---|---|---|
| | 300 N | 535 N |
| Screw Hole | 32.4 M Pa | 57.8 M Pa |
| Highest Stress at any other point | 37.3 M Pa | 66.5 M Pa |

EXAMPLE IX

A bone plate was fabricated of the design shown in FIG. 6-10. The plate had a unreinforced thickness of 5 millimeters and a top reinforcement of 2.6 millimeters. The plate was 12 millimeters wide and had a side reinforcement of 3.2 millimeters, 1.6 millimeters on each side. The plate was 73.20 millimeters in length and had six screw holes spaced 12 millimeters from center line to center line with a space of 15 millimeters between the center holes. The plate was loaded with a force of 300 Newtons. in a three point bending configuration with the force applied at a screw hole. The stresses developed were:

| Location | Stress M Pa |
|---|---|
| $S_2a$ | 14.26 |
| $S_2'a$ | 31.81 |
| $S_2'b$ | 29.67 |
| $S_2b$ | 22.39 |
| $S_1$ | 31.1 |

The force was increased to 535 Newtons and the stresses determined

| Location | Stress M pa |
|---|---|
| $S_2a$ | 25.41 |
| $S_2'a$ | 56.79 |
| $S_2'b$ | 52.97 |
| $S_2b$ | 39.96 |
| $S_1$ | 55.52 |

What is claimed:

1. An absorbable bone plate comprising an elongated bar-like body having a lower surface, an upper surface, opposite sides and opposite ends, a plurality of screw holes extending through said plate from the upper surface through the lower surface, the width of the plate being extended around the screw holes as a reinforcement and in which the thickness of the plate is extended on the upper surface of the plate in an arcuate shape around the screw holes as a reinforcement area so that the stresses developed around the screw holes on implantation are not significantly greater than the highest stresses developed in any unreinforced area of the plate, and in which the dimensions of the plate meet the limitations:

$$\sqrt{W^2 + R_1^2} \leq R \leq \sqrt{W^2 + (L/2)^2} \quad \text{(a)}$$

$$r \geq \sqrt{R_1^2 + H} \quad \text{(b)}$$

$$d'_2 > d_2 \quad \text{(c)}$$

$$d_2 = \sqrt{R^2 - W^2} \quad \text{(d)}$$

$$d'_2 = \sqrt{r^2 - [\sqrt{r^2 - R_1^2} - H]^2} \quad \text{(e)}$$

$$h = r_2 - \sqrt{r_2^2 - W^2} \quad \text{(f)}$$

where:

W is one half the width of the unreinforced plate

R is the radius of the side reinforcement of the plate measured from the centerline of a screw hole H is the height of the top reinforcement measured from the unreinforced top surface of the plate r is the radius of the top reinforcement of the plate measured from a point on the centerline of a screw hole $d'_2$ is the distance from the centerline of the screw hole to the point where the top reinforcement intersects the unreinforced top of the plate $d_2$ is the distance from the transverse centerline of the screw hole to the point where the side reinforcement intersects the unreinforced side of the plate L is the distance between adjacent screw holes measured from the screw hole centerlines $R_1$ is the radius of the countersink measured from the screw hole centerline $r_2$ is the radius of curvature of the bottom of the plate k is the minimum unreinforced thickness of the plate measured from the top of the radius of curvature of the bottom of the plate to the unreinforced top of the plate T is the unreinforced plate thickness at the side edge of the plate h is the difference between T and k.

2. The bone plate of claim 1 in which the top of the reinforced area of the plate around the screw holes is flattened and countersunk around the screw holes.

3. The bone plate of claim 1 in which the top reinforced area is a section of a sphere.

4. The bone plate of claim 1 in which the top reinforced area is a section of the right cylinder having an axis along the transverse centerline of the screw hole.

5. The bone plate of claim 1 in which the stresses in the plate across a screw hole where the plate is attached to bone is not different by more than 20% from the highest stresses developed anywhere else in the plate up to the next screw hole when the plate is subjected to force.

6. The bone plate of claim 1 in which the stresses in the plate across a screw hole where the plate is attached to bone is not different by more than 10% from the highest stresses developed anywhere else in the plate up to the next screw hole when the plate is subjected to force.

7. The bone plate of claim 4 in which the stresses in the plate across a screw hole where the plate is attached to bone is not different by more than 20% from the highest stresses developed anywhere else in the plate up to the next screw hole when the plate is subjected to force.

8. The bone plate of claim 4 in which the stresses in the plate across a screw hole where the plate is attached to bone is not different by more than 10% from the highest stresses developed anywhere else in the plate up to the next screw hole when the plate is subjected to force.

* * * * *